(12) United States Patent
DeHarde

(10) Patent No.: US 9,377,079 B2
(45) Date of Patent: Jun. 28, 2016

(54) BI-DIRECTIONAL DAMPENING AND ASSISTING UNIT

(71) Applicant: Ultraflex Systems, Inc., Pottstown, PA (US)

(72) Inventor: Mark DeHarde, Pottstown, PA (US)

(73) Assignee: Ultraflex Systems, Inc., Pottstown, PA (US)

( * ) Notice: Subject to any disclaimer, the term of this patent is extended or adjusted under 35 U.S.C. 154(b) by 183 days.

(21) Appl. No.: 14/249,511

(22) Filed: Apr. 10, 2014

(65) Prior Publication Data

US 2014/0308065 A1 Oct. 16, 2014

Related U.S. Application Data

(60) Provisional application No. 61/810,412, filed on Apr. 10, 2013.

(51) Int. Cl.
*F16C 11/00* (2006.01)
*F16F 15/04* (2006.01)
*A61F 5/01* (2006.01)

(52) U.S. Cl.
CPC ............... *F16F 15/04* (2013.01); *A61F 5/013* (2013.01); *A61F 5/0125* (2013.01);
(Continued)

(58) Field of Classification Search
CPC ............... Y10T 403/32557; Y10T 403/32591; Y10T 403/32598; Y10T 403/32606; Y10T 403/32614; Y10T 403/32803; Y10T 403/32811; Y10T 403/32819; Y10T 403/32827; Y10T 29/49826; Y10T 16/54028; Y10T 16/540256; Y10T 16/540257; A61F 2005/0139; A61F 2005/0167; A61F 2005/0165; A61F 2005/0179; A61F 5/01; A61F 5/0125; A61F 5/013; A61F 5/058; A61F 2002/5043; A61F 2002/5098; F16F 15/04; F16F 1/14; F16F 2238/024; F03G 2730/03; B21D 39/00
USPC ............ 403/113, 117–120, 143–146; 602/16, 602/20, 26, 27; 267/154, 155, 273
See application file for complete search history.

(56) References Cited

U.S. PATENT DOCUMENTS

| | | | | |
|---|---|---|---|---|
| 411,235 | A | * | 9/1889 | Remington ............. B27B 27/02 83/438 |
| 4,087,885 | A | * | 5/1978 | Gillentine ............ B60N 2/2356 16/325 |

(Continued)

OTHER PUBLICATIONS

International Search Report and Written Opinion dated Aug. 26, 2014; International Application No. PCT/US2014/033617; International Filing Date: Apr. 10, 2014; 7 pages.

*Primary Examiner* — Gregory Binda
*Assistant Examiner* — Nahid Amiri
(74) *Attorney, Agent, or Firm* — Blank Rome LLP

(57) ABSTRACT

A dynamic platform with extending struts has fastened thereto a bi-directional torsional power unit to selectively deliver force opposing either extension or flexion, and to provide assistance in a respective opposite direction. The power unit is threadably mounted on a hinge pin (spline) centrally located on the platform, and is latched to a catch assembly radially located thereto, the hinge pin of the platform communicating with one end of a torsion spring of the power unit and the catch assembly communicating with another end of the torsion spring, to selectively deliver the extension/flexion force. The power unit can be detached, with simple manual operation of the catch assembly, without tools, flipped over and reattached to the same platform attachment points to switch (reverse) extension torque to flexion torque and vice versa.

20 Claims, 10 Drawing Sheets

(52) U.S. Cl.
CPC  *A61F 2005/0139* (2013.01); *A61F 2005/0167* (2013.01); *A61F 2005/0179* (2013.01); *Y10T 403/32557* (2015.01)

(56) References Cited

U.S. PATENT DOCUMENTS

| | | | | |
|---|---|---|---|---|
| 4,433,679 A * | 2/1984 | Mauldin | ............... | A61F 5/0125 602/16 |
| 4,625,943 A * | 12/1986 | Groger | ............... | F02M 19/128 251/305 |
| 4,697,673 A * | 10/1987 | Omata | ............... | E05F 3/14 16/52 |
| 4,846,842 A * | 7/1989 | Connolly | ............... | A61F 5/0125 602/16 |
| 5,031,606 A * | 7/1991 | Ring, Sr. | ............... | A61F 5/0125 602/16 |
| 5,036,837 A | 8/1991 | Mitchell et al. | | |
| 5,052,379 A * | 10/1991 | Airy | ............... | A61F 5/0125 482/112 |
| 5,086,760 A * | 2/1992 | Neumann | ............... | A61F 5/0123 602/16 |
| 5,328,446 A * | 7/1994 | Bunnell | ............... | A61F 5/0125 482/131 |
| 5,472,410 A * | 12/1995 | Hamersly | ............... | A61F 5/0125 601/33 |
| 5,658,241 A | 8/1997 | DeHarde et al. | | |
| 5,830,166 A | 11/1998 | Klopf | | |
| 6,471,664 B1 | 10/2002 | Campbell et al. | | |
| 6,565,523 B1 * | 5/2003 | Gabourie | ............... | A61F 5/0125 602/16 |
| 6,872,187 B1 * | 3/2005 | Stark | ............... | G06F 19/3418 482/8 |
| 7,517,330 B2 * | 4/2009 | Deharde | ............... | A61F 5/0125 602/16 |
| 7,553,289 B2 * | 6/2009 | Cadichon | ............... | A61F 5/0123 602/23 |
| 8,052,216 B2 * | 11/2011 | Nathan | ............... | B60N 2/206 297/332 |
| 8,257,283 B2 * | 9/2012 | Kaiser | ............... | A61H 1/0285 601/33 |
| 2006/0211966 A1 * | 9/2006 | Hatton | ............... | A61F 5/0125 602/16 |
| 2011/0098828 A1 | 4/2011 | Balboni et al. | | |
| 2013/0283620 A1 * | 10/2013 | Snyder | ............... | F16F 1/06 30/159 |

* cited by examiner

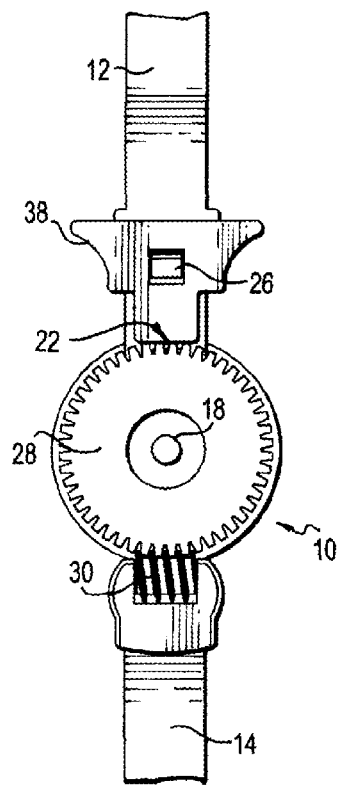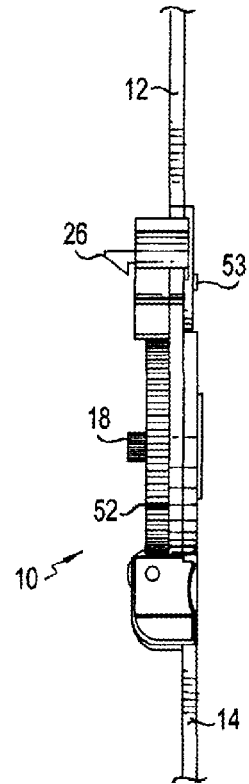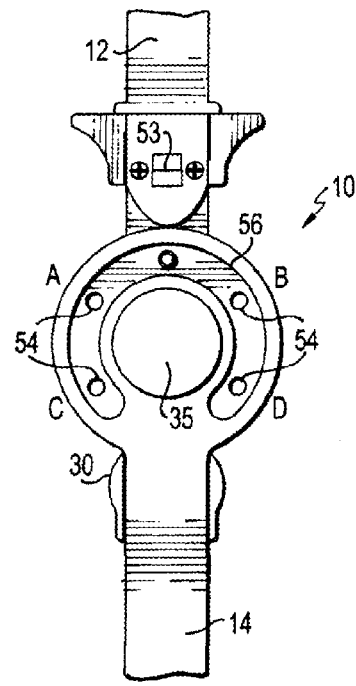
FIG. 9a
FIG. 9a'
FIG. 9b

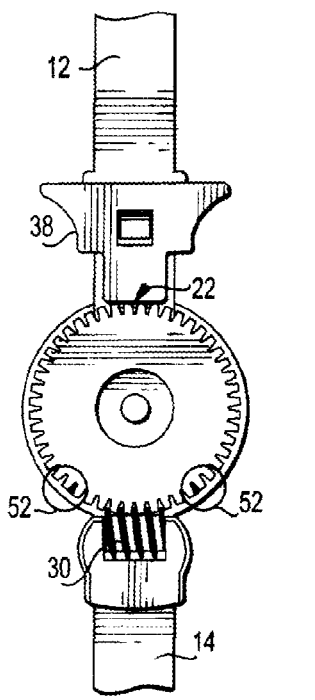 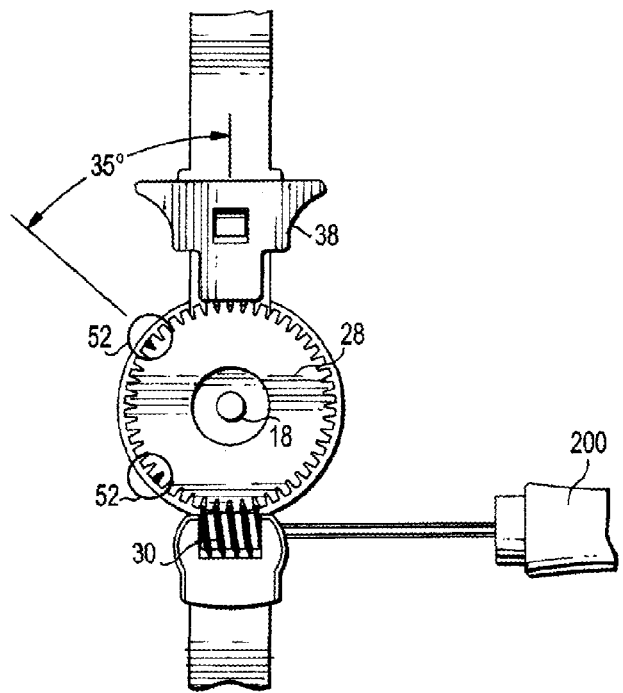
FIG. 11a    FIG. 11b
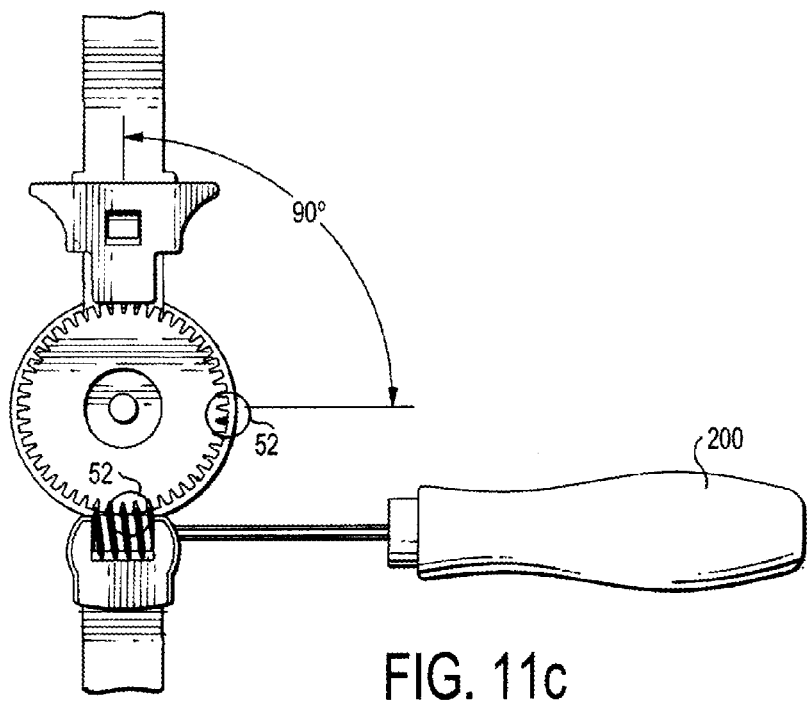
FIG. 11c

BI-DIRECTIONAL DAMPENING AND ASSISTING UNIT

RELATED APPLICATION

This application claims benefit of priority of U.S. Provisional Application No. 61/810,412, filed Apr. 10, 2013, entitled "Bi-Directional Dampening/Assisting Unit." The above-identified related application is incorporated herein by reference.

FIELD OF THE INVENTION

The present invention relates generally to hinge or joint devices generally, and more particularly to a hinge or joint assembly, at the ankle, wrist, knee or ankle, adapted to exert a bi-directional force at the body joint to provide dynamic shock absorption and return assistance, while enabling normal, or close to normal, ambulatory motion.

BACKGROUND OF THE INVENTION

To treat flexion and extension contractures, spring-biased splint units have been developed to provide a force across a body joint. These splint devices provide tension that operates in opposition to a flexion or extension contracture and thereby not only provide support in instances where muscular weakness exists, but also enhance rehabilitation. Generally, treatment involves lengthening short muscles and reducing soft tissue contracture caused by various pathologies that result in joint movement limitations. In one example, two struts are pivotally interconnected, and include a spring bias unit therebetween to apply an adjustable force at the pivot point of the interconnected struts.

For helpful background information, U.S. Pat. No. 5,658,241 to DeHarde includes a prior teaching, generally, of torsional power units, multi-functional dynamic splints, spring bias adjustment mechanisms, range of motion limiters, and early bi-directional functionality. DeHarde, U.S. Pat. No. 5,658,241, is incorporated herein by reference for its helpful detailed description of the various assembly components, their interaction and functionality, all providing a better appreciation and background for the present invention. More particularly, U.S. Pat. No. 5,658,241, teaches a dynamic splint using a bi-directional torsional power unit fastened between first and second struts to selectively deliver force opposing either extension or flexion. In U.S. Pat. No. 5,658,241, the power unit is mounted about a hinge pin and can be rotated about the hinge pin between two positions. In a first position, the power unit is locked relative to the first strut and the torsion spring opposes relative movement of the second strut in a first direction. Rotated about the hinge pin to a second position, the power unit is locked relative to the second strut. In this second position, the torsion spring opposes movement of the first strut relative to the second strut, providing torsion in an opposite direction from that of the first position.

SUMMARY OF THE INVENTION

The present invention is a hinge assembly providing a dynamic, universal platform, with struts extending therefrom, having attached thereto a bi-directional, torsional power unit to selectively deliver force opposing either extension or flexion. The power unit includes a torsion spring, such as a circular leaf spring. In the present invention, the power unit can be easily reversed to provide a flexion or extension force for any human joint by simply flipping the power unit over and snapping the power unit back into place on the platform. The power unit is mounted on a hinge pin (spline) of the platform, and also attaches to a tab, pin or latch communicating with one of the struts.

The present invention hinge assembly (combination dynamic platform and power unit) provides a slimmer, lighter, lower profile design with increased functionality and more adaptable torque characteristics. The present invention could, for example, be a hinge assembly for an orthotic, prosthetic or rehabilitative device; or generally be a hinged splint type device for applying force across a body joint.

Further, the present invention provides a platform having unique worm gear range of motion (ROM) limiters able to infinitely limit any angular joint displacement required to either correspond to or exceed the desired body joint motion. The worm gear ROM limiters can work in conjunction with hard stops placed in arcuate slot. In various embodiments, one or two worm gears might be employed on the platform to limit range of motion. In any embodiment, the platform of the present invention can be easily set for an elbow, knee, ankle or wrist human joint. In view thereof, any limit on the range of motion (within the typical range of motion for the respective body joint) can be set, in both directions—extension or flexion. Further, the platform can provide a locking feature for any 7.5 degree of motion, or any 15 degree of motion, and also provide a free motion option for ease of donning and doffing of the associated brace. In another aspect of the invention, two platform sizes (and two power unit sizes) can facilitate any human body joint, a complete range of motion thereof, and various torque resistances/assistances.

As mentioned above, reversing extension torque into flexion torque can be accomplished by flipping the power unit over. The spline interface between the platform and the power unit permits a user to match the range of motion needed for the desired body joint to that possible by the present invention. Accordingly, the desired range of motion of the body joint can be matched to the total spring deflection possible for the power unit to yield a torque over that same range of motion to either provide a desired flexion or extension force. The spline of the platform transmits torque from the power unit to rotate the platform (i.e., to angularly move the struts relative to one another) and the associated brace attached thereto to yield a desired clinical benefit.

In one aspect of the present invention, the power unit allows for 150 degrees of torque resist/assist and the spline orients this torque resist/assist range of motion to the desired range of the platform. Each spline tooth can shift the range of motion 15 degrees to enable this advantageous feature. The spline connection (i.e., power unit mounted on the spline of the platform) could be used to transmit any force creating mechanism (i.e., power unit) to a joint (i.e., platform) having a strut arrangement to control, assist or dampen the struts, and therefore control, assist or dampen any movement of the respective body joint.

In one general embodiment of the present invention, a hinge assembly includes a first strut and a second strut pivotally attached to one another at a pivot point. A spline generally extends in a first direction perpendicularly through the first strut and the second strut and serves as the pivot point. The spline can be rotatably fixed relative to one of the first strut and the second strut, the other of the first strut and the second strut has a single catch extending in the first direction, located radially of the pivot point. Also included is a torsion spring having a first end and a second end, where the first end of the torsion spring is removably attached to the extending spline and the second end of the torsion spring is removably attached to the single extending catch.

The torsion spring applies a bias force opposing relative pivotal movement between the first and the second struts in a first of two opposite directions, and aids pivotal movement in a second of the opposite directions. The torsion spring can be detached from the extending spline and the single extending catch, turned over, and re-attached. Re-attachment involves again connecting the first end of the torsion spring to the extending spline and the second end of the torsion spring to the single extending catch. A bias force opposing relative pivotal movement between the first and the second struts in the second of the opposite directions is then applied, along with assistance of pivotal movement in the first of the opposite directions.

The hinge assembly can also include a toothed tension wheel mounted about the pivot point and rotatably fixed relative to the spline, and an axially rotatable, but otherwise fixed, worm gear located about a perimeter of the tension wheel, the worm gear threadably communicating with the tension wheel to preload the torsion spring.

In another embodiment of the present invention, the hinged device used to apply force across a body joint includes a platform having a first strut, a second strut; and a joint assembly having a threaded spline at a pivot point thereof. The threaded spline is workably fixed to one of the first strut or the second strut—the other of the first strut or the second strut has a catch located radially of the pivot point, the first strut and the second strut pivoting relative to one another about the pivot point.

The hinged device also includes a power unit having a torsion spring, and a housing having an internally threaded reception slot centrally located on each of opposing housing sides of the power unit. The reception slot is workably attached to a first end of the torsion spring. The housing also has a catch receiver similarly located on each of opposing housing sides of the power unit, the catch receiver being workably attached to a second end of the torsion spring.

In this embodiment, when a first housing side is exposed away from and opposite the platform, the power unit attaches to the platform to apply a bias force opposing relative pivotal movement between the first and the second struts in a first of two opposite directions, and aiding pivotal movement in a second of the opposite directions. When a second housing side is exposed away from and opposite the platform, the power unit attaches to the platform to apply a bias force opposing relative pivotal movement between the first and the second struts in the second of the opposite directions, and aiding pivotal movement in the first of the opposite directions.

The power unit can be detached, flipped over and reattached to the platform (reversed), without the use of tools. The power unit is flipped over from the first housing side being exposed away from and opposite the platform to the second housing side being exposed away from and opposite the platform. Reversing the power unit on the platform is accomplished without taking apart a spring housing, or requiring dismantling of a spring device. Nor does reversing the power unit on the platform (reversing the direction of force) require use of a different spring(s), or the re-installation of the spring in different holes or at different contact points (points of attachment) on the platform.

In the present invention, points of attachment between the power unit and the platform can consist only of the one centrally located reception slot on each housing side of the power unit, the one spline of the platform, the one catch receiver similarly axially located on each housing side of the power unit, and the one catch on the platform located radially of the pivot point.

In another aspect, the hinged device of the present invention can also include an axially translatable handle that toothedly engages a gear centered about the pivot point to arrest pivotal movement of the first strut relative to the second strut. The power unit could also include an externally threaded spring band located about a perimeter of the torsion spring, centered about the pivot point, and workably attached to the second end of the torsion spring, and an axially rotatable, but otherwise fixed, preload worm gear located about a perimeter of the spring band, the preload worm gear threadably communicating with the spring band to preload the torsion spring. The torsion spring, spring band and the worm gear could be positioned in the same plane.

The catch of the present invention device could extend perpendicularly from the respective strut, and include at a distal end thereof a lip extending perpendicularly toward the pivot point, the catch being spring biased toward the pivot point and linearly translatable along a longitudinal axis of the respective strut. The catch receiver could be an aperture similarly and opposingly located on each housing side of the power unit. The spring biased catch could cause a snap connection of the lip to the aperture when the power unit is attached to the platform. If also including the axially translatable handle, the catch could extend perpendicularly from the respective strut from within, and be surrounded by, the axially translatable handle.

In another aspect, the present invention platform might further have a toothed range of motion (ROM) wheel mounted about the pivot point and rotatable relative to the first and the second struts; and an axially rotatable, but otherwise fixed, ROM worm gear located about a perimeter of the ROM wheel. The ROM worm gear threadably communicates with the ROM wheel to adjust a range of motion of the first strut relative to the second strut.

The joint assembly of the present invention might also include at least one end range tapped hole rotatably fixed relative to one of the first and the second struts, at least one end range screw, inserted into and extending from the at least one end range tapped hole, and an arcuate slot rotatably fixed relative to the other of first and the second struts. The at least one end range screw extends into the arcuate slot to limit range of motion the device. Here, the platform provides up to a 150° range of motion of the first and the second struts.

In this joint assembly embodiment, a position of the at least one end range tapped hole, with the at least one end range screw inserted therein, allows motion of the at least one end range screw within the arcuate slot from 135° of flexion to 15° of hyperextension. This provides a correct anatomical range of motion for a knee. At least a second end range tapped hole could also be included, each end range tapped hole having a position, where, with end range screws inserted therein, allows motion of the end range screws within the arcuate slot of 75° of plantar flexion to 75° of dorsiflexion to provide a correct anatomical range of motion for a wrist or ankle. The joint assembly might also include the toothed range of motion (ROM) wheel and ROM worm gear, detailed above, to adjust a range of motion of the first strut relative to the second strut within the fixed limits established by the at least one end range tapped hole, the at least one end range screw, and the arcuate slot.

The ROM wheel could also include at least two stop angle marks on a perimeter thereof, one mark corresponding to an extension range limit and another mark corresponding to a flexion range limit. Here, the ROM worm gear is used to rotatably position one of the stop angle marks at an angle relative to a midline of the first strut to finely adjust device range of motion, wherein platform angular motion is limited to the angle in a respective flexion or extension range. In this embodiment, the ROM worm gear can function to finely adjust device range of motion with the power unit attached to or detached from the platform.

Also included in the present invention is a method of reversing an angular direction of force applied by and above detailed hinge assembly embodiment, the method including the steps of linearly translating the catch along a longitudinal axis of the other of the first strut or the second strut, away from the pivot point and against the spring bias of the catch; pulling the power unit in a direction perpendicular of the first and the second struts, lifting the power unit off of the spline to detach the power unit from the platform; turning (flipping) the power unit over; threadably engaging the reception slot of the housing with the spline while aligning the catch receiver of the housing with the catch, without the use of tools, and without requiring use of any other point of attachment on or between either the platform or the power unit; and pressing the power unit against the platform until the spring biased catch causes snap connection of the catch to the catch receiver. The above steps attach the power unit to the platform to apply a bias force opposing relative pivotal movement between the first and the second struts in a direction opposite that of the force applied prior to turning (flipping) the power unit over, and aiding pivotal movement in a direction opposite of that provided prior to turning the power unit over.

BRIEF DESCRIPTION OF THE ILLUSTRATED EMBODIMENTS

The present invention will be better understood with reference to the following description taken in combination with the drawings. For the purpose of illustration, there are shown in the drawings certain embodiments of the present invention. In the drawings, like numerals indicate like elements throughout. It should be understood, however, that the invention is not limited to the precise arrangements, dimensions, and instruments shown:

FIG. 1 illustrates a bi-directional dampening/assisting unit according to one embodiment of the present invention, including power unit attached to a platform, where the power unit provides extension or flexion torque upon respective angular movement of struts extending from the platform, and where the power unit can be flipped over to switch from extension torque to flexion torque, or vice versa, in the respective angular direction;

Figure 1:
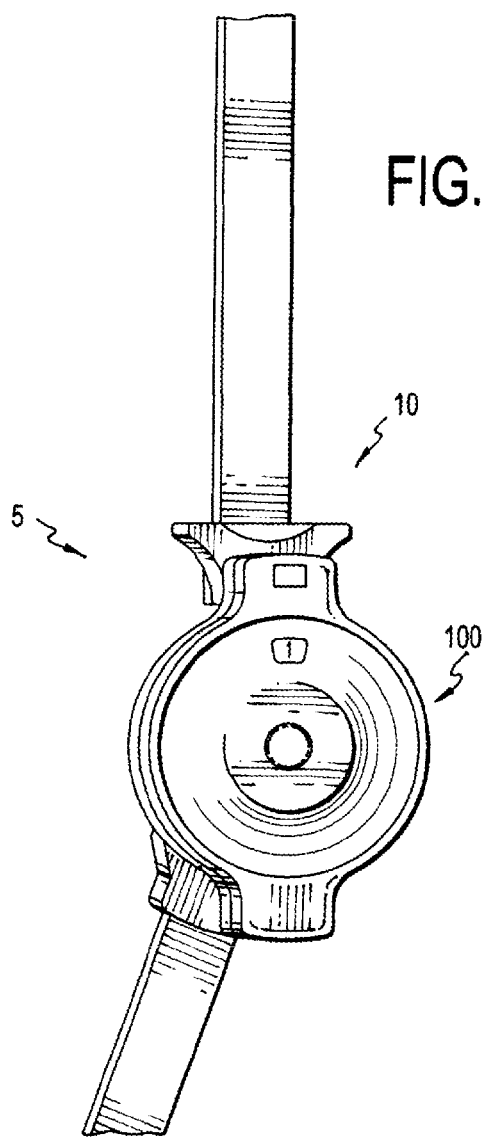
Figure 5:
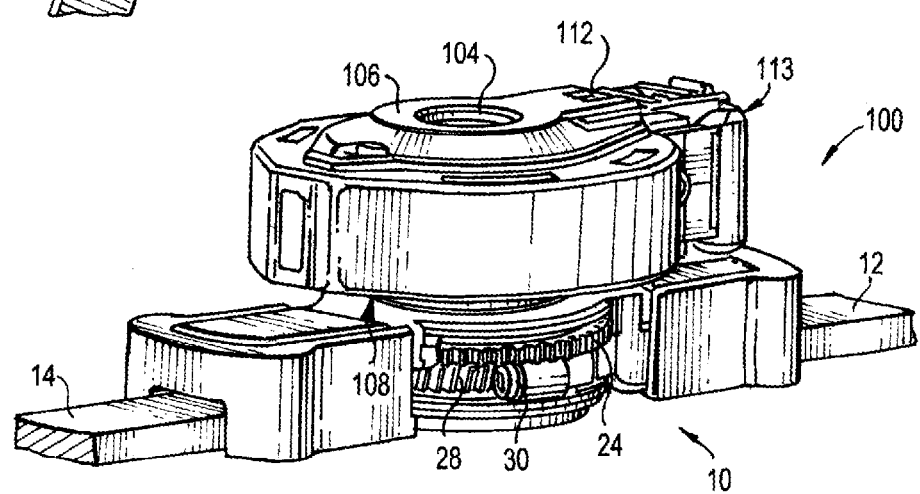
Figure 4:
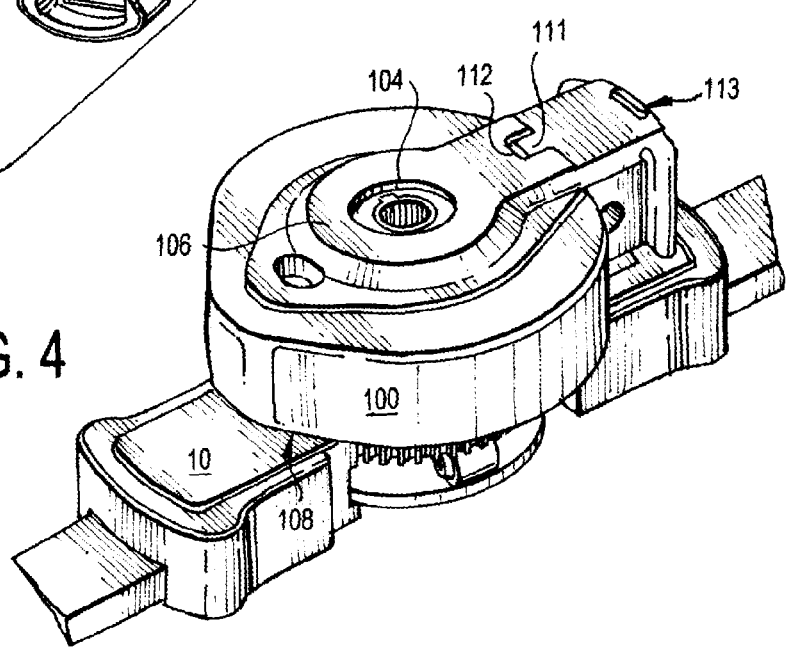
Figure 6:
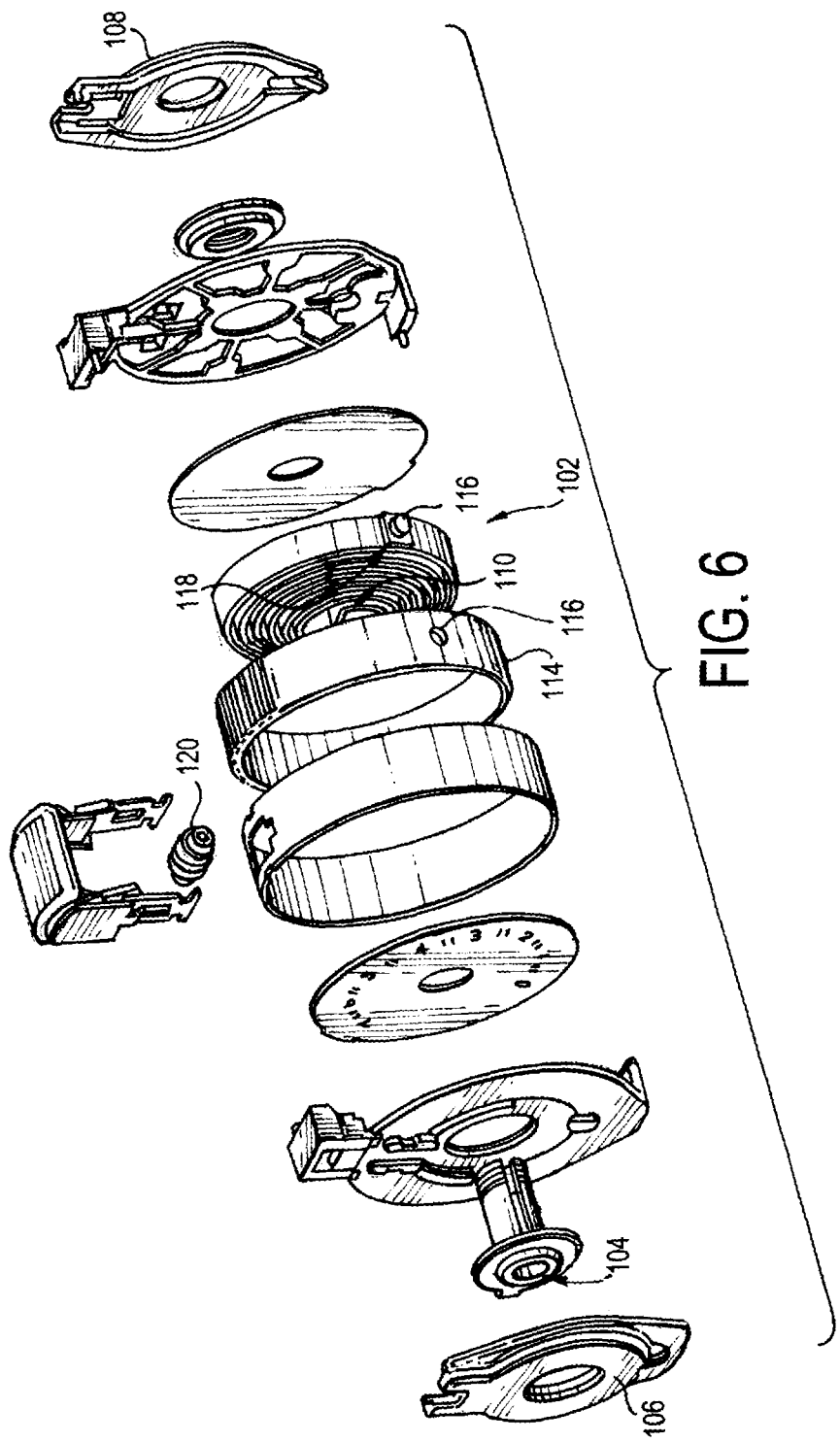
Figure 7A:
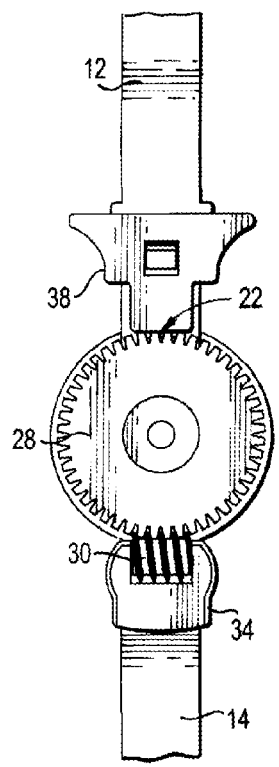
Figure 7B:
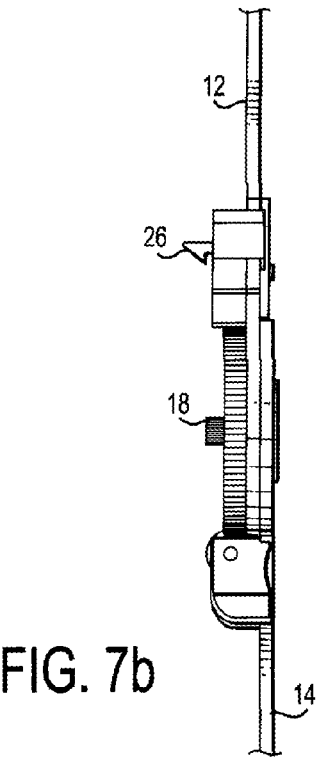
Figure 7C:
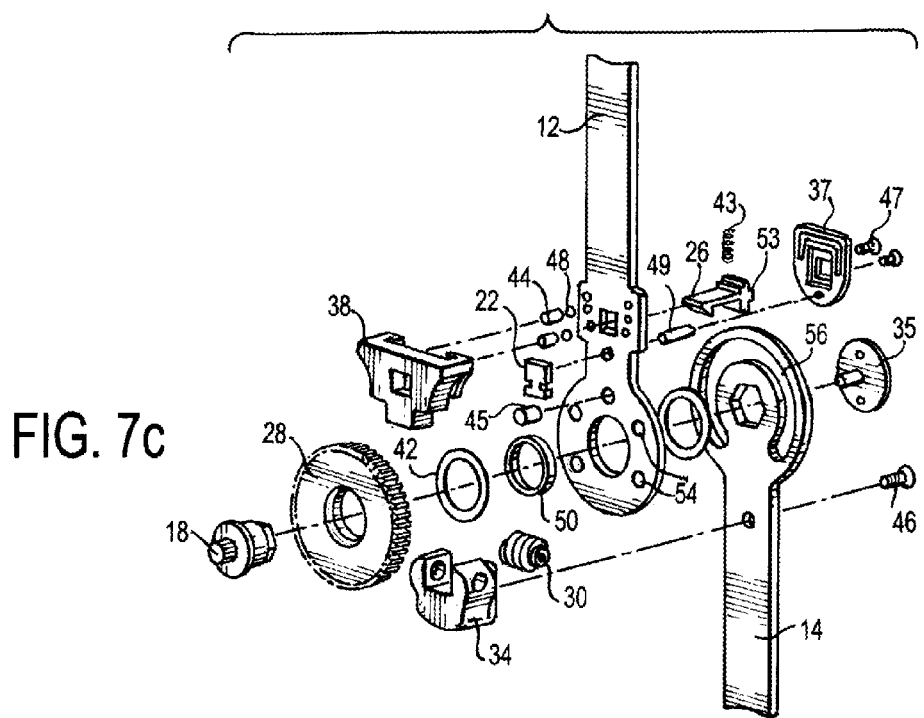
Figure 8A:
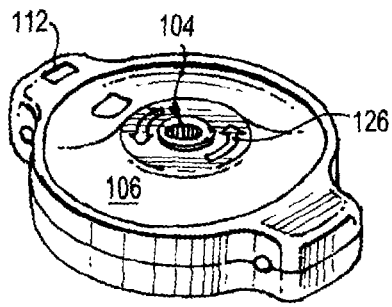
Figure 8B:
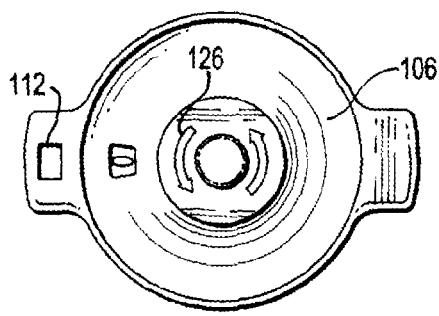
Figure 8C:
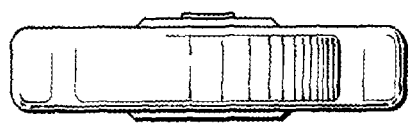
Figure 8D:
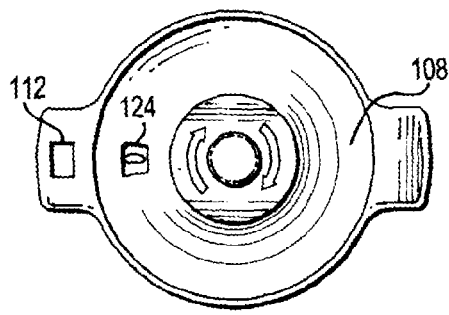
Figure 8E:
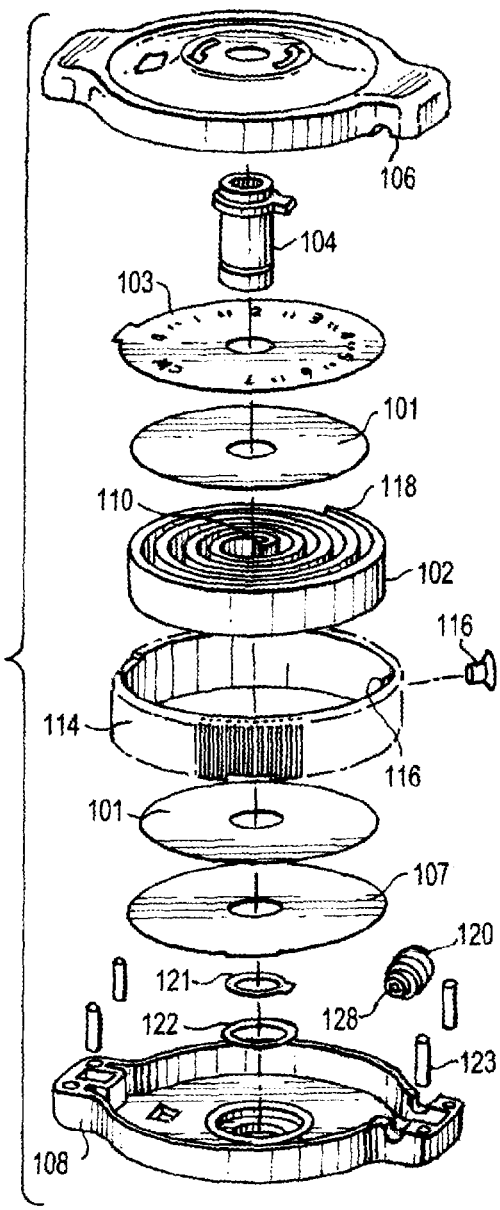
Figure 10A:
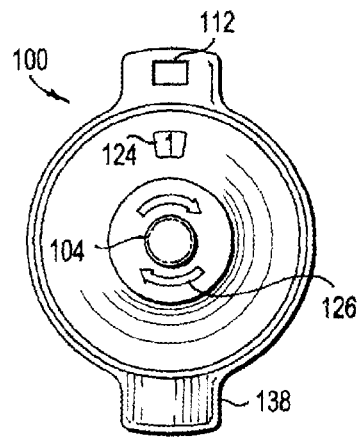
Figure 10B:
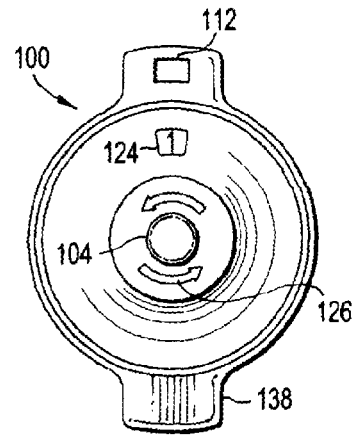

FIG. 4 illustrates a bi-directional dampening/assisting unit according to another embodiment of the present invention, again including power unit attached to a platform of the present invention, where the power unit provides extension or flexion torque upon respective angular movement of struts extending from the platform, and where the power unit can be flipped over to switch from extension torque to flexion torque, or vice versa, in the respective angular direction;

FIG. 5 illustrates a side view of the bi-directional dampening/assisting unit of FIG. 4, with power unit attached to the platform; and FIG. 6 illustrates the power unit of FIGS. 4 and 5 in exploded view;

FIGS. 7a, 7b and 7c illustrate a front, side and exploded view, respectively, of another embodiment of the platform 10 of the present invention (i.e., the platform 10 shown in FIG. 1);

FIGS. 8a, 8b, 8c, 8d and 8e illustrate perspective, top side, edge, opposite side and exploded views, respectively, of another embodiment of the power unit 100 of the present invention (i.e., the power unit 100 shown in FIG. 1);

FIGS. 9a, 9a' and 9b illustrate a front profile, a side profile and a reverse profile of the platform 10 embodiment of FIGS. 1, 7a, 7b, and 7c;

FIGS. 10a and 10b illustrate a front profile and a reverse profile of the power unit 100 embodiment of FIGS. 1, 8a, 8b, 8c, 8d and 8e;

FIGS. 11a, 11b and 11c illustrate fine tuning of the platform 10 embodiment of FIGS. 1, 7a, 7b, 7c, 9a 9a' and 9b, to block excessive or unwanted flexion or extension range of motion; and FIGS. 12a, 12b, 12c, 12d and 12e illustrate how to use the bi-directional dampening/assisting unit of FIG. 1; more specifically, how to set up the platform 10 and attach the power unit 100 thereto for certain flexion/extension assist.

DETAILED DESCRIPTION OF THE ILLUSTRATED EMBODIMENTS

The present invention provides a dynamic platform, having struts extending therefrom, and having fastened thereto a bi-directional torsional power unit, between first and second struts. The torsional power unit selectively delivers force opposing either extension or flexion, while providing assistance in a respective opposite direction. The torsional power unit is mounted on a hinge pin (spline) extending from a pivot point of the platform, where the power unit can be flipped over to switch (reverse) the force opposing extension or flexion to the respective other thereof.

FIG. 1 illustrates a bi-directional dampening/assisting unit 5 according to one embodiment of the present invention, including power unit 100 and platform 10. FIGS. 2-3 illustrate a platform 10 of the present invention including a first and a second strut 12, 14 interconnected at a pivot point 16, with threaded spline 18 extending therefrom, FIG. 3 illustrating an exploded view. The threaded spline 18 is rotationally fixed in relation to the second strut 14. The pivot point and components of the platform other than the struts 12, 14 form a joint assembly.

Figure 2A:
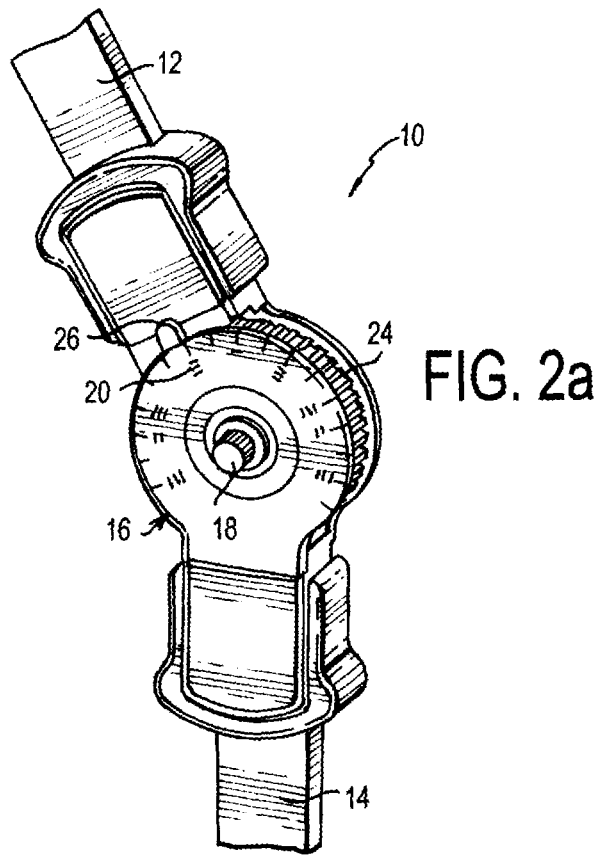
FIG. 2a illustrates a platform according to an embodiment of the present invention that includes two struts interconnected at a pivot point, with threaded spline extending therefrom, where the struts are located in one working position.
Figure 2B:
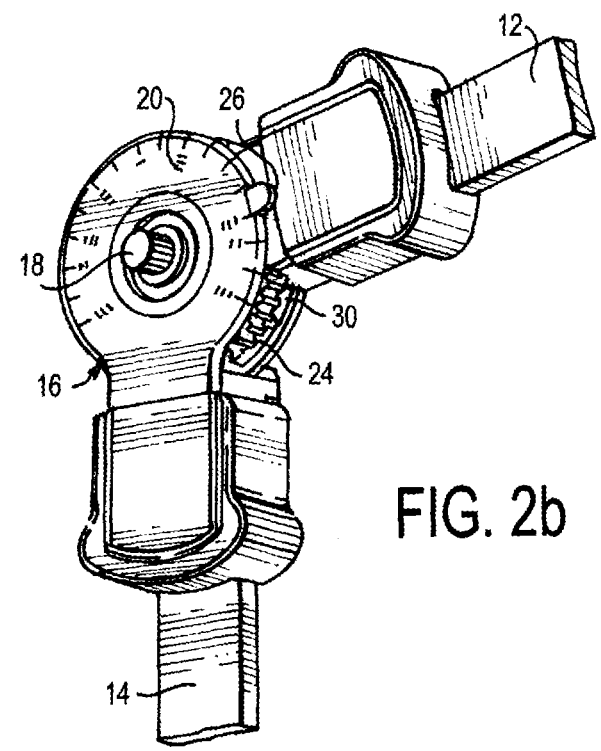
FIG. 2b illustrates the platform of FIG. 2a, where the struts are located in another working position.
Figure 3:
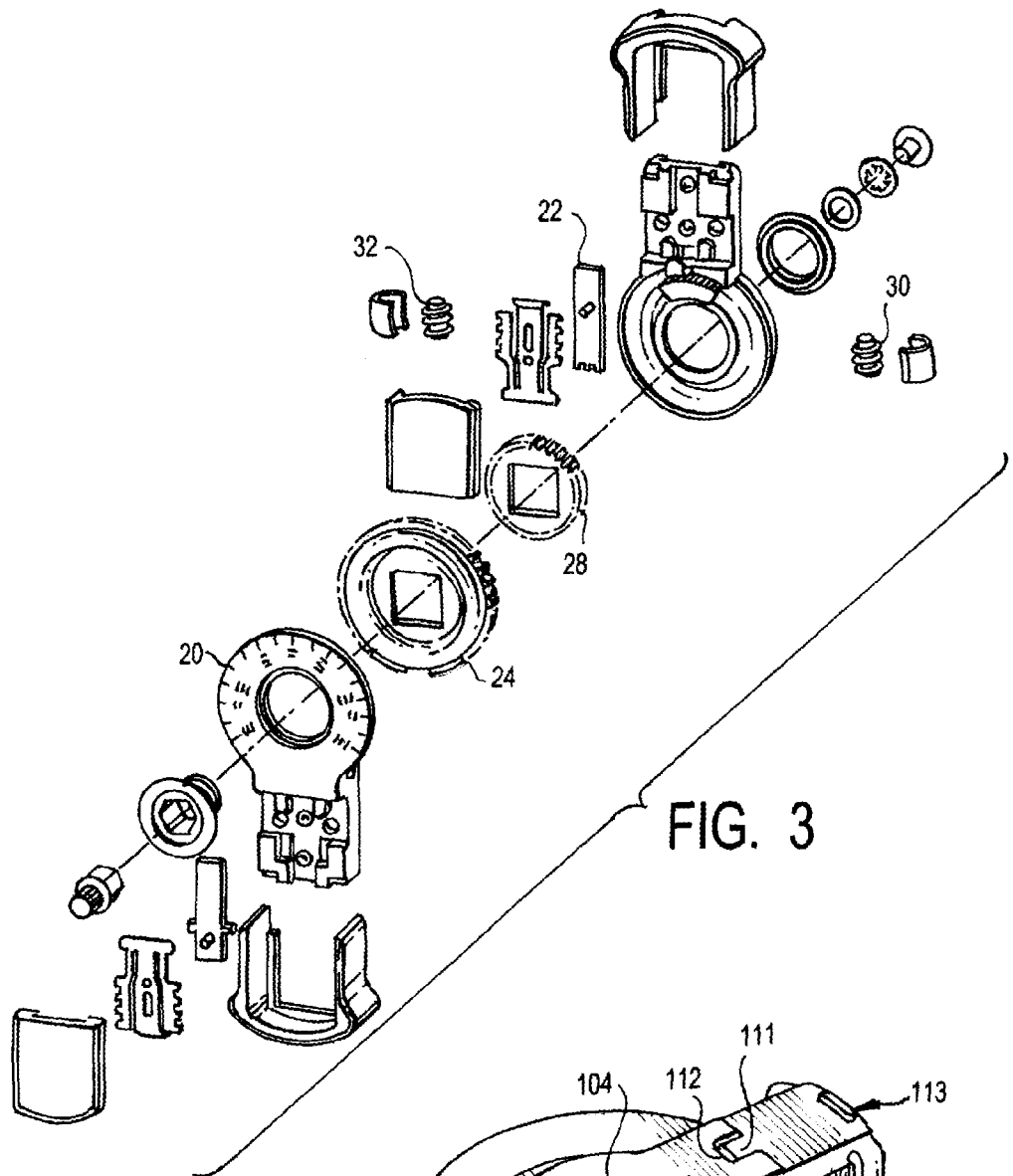
FIG. 3 illustrates the platform of FIGS. 2a and 2b in exploded view.

FIG. 2a illustrates the platform 10 in one working position, aligned for use (range of motion (ROM) appropriate for) a knee or elbow joint. Alignment of the platform 10 is shown by graduated markings 20 posted on a side of the platform 10. Alignment of the platform is performed by manual operation of a toothed disk 22, associated and aligned with the first strut 12, to linearly translate the toothed disk 22 in relation to the first strut 12 to engage a stationary and toothed alignment wheel 24. FIG. 2b illustrates the platform in another working position, aligned for use (range of motion appropriate for) an ankle or wrist. In one embodiment, each graduated marking represents 15 degrees, which is equal to the degree range associated with each thread of the spline 18.

Alignment is shown by a tab or pin 26. The tab 26 is fixed in relation to, and extends at a relative distal end location of, the first strut 12. Accordingly, the first strut 12 and the second strut 14 communicate with the joint assembly, providing that the first strut 12 can pivotally move relative to the second strut 14 about the pivot point 16.

Referring now to FIG. 3, the platform 10 further includes a stationary and toothed range of motion (ROM) wheel 28. Two worm gears 30, 32, each communicating with, and movable in relation to, a perimeter of the ROM wheel 28, provide range of motion stops (or limiters) for the platform 10. Accordingly, the pivotal range of motion of one strut (e.g., the first strut 12) relative to the other strut (e.g., the second strut 14) is limited by a relative position of each worm gear 30, 32, acting as a strut stop, about the perimeter of the ROM wheel 28. Axial rotation of each worm gear 30, 32, respectively indexes (translates) the respective worm gear about the perimeter of the stationary ROM wheel 28.

FIGS. 4-6 illustrate a power unit 100 of the present invention attached to a platform 10 of the present invention, whereby the power unit 100 provides extension or flexion torque upon respective angular movement of the struts 12, 14. FIG. 6 illustrates an exploded view. The power unit 100 can be flipped over on the platform 10 to switch from extension torque to flexion torque, or vice versa, in a respective direction.

The power unit 100 includes a torsion spring 102 (e.g., a circular leaf spring) and a internally threaded reception slot 104 open to, and centrally located on, each of opposing sides of the power unit 100 (i.e., open to, and centrally located within, each of opposing housing side plates 106, 108). The respective reception slot 104 communicates with a first end 110 of the torsion spring 102.

The power unit 100 threadably attaches to the platform 10 via the spline 18 and the reception slot 104 open on a first side housing plate 108 of the power unit 100 (as shown in FIGS. 4 and 5) to apply a bias force opposing relative pivotal movement between the first and the second struts 12, 14 in a first of two opposite directions and aiding such pivotal movement in a second of the opposite directions. Facilitating the bias force is a second attachment of the power unit 100 to the platform 10, occurring between tab 26 and tab reception aperture 112. A tab reception aperture 112 is also located on each of opposing sides of the power unit 100 (i.e., on each housing side plate 106, 108).

In one embodiment, the tab 26 includes a shelf, or 90 degree lip (as best shown in FIG. 2b), creating a latch mechanism. The tab reception aperture 112 includes, at an outer edge (near to the top) thereof, a movable (slidable) door 111 adapted to slide over the tab reception aperture 112 and catch (latch) to the lip or shelf of the tab 26. The slidable door 111 is operable from, and communicates with, a spring biased, slidably translatable sliding bar 113, which extends from a center area of the power unit 100. Translating the sliding bar 113 away from the center of the power unit 100 fully opens the tab reception aperture 112 to receive the 90 degree angled tab 26. Releasing the sliding bar, via spring bias closing, returns the slidable door towards the center of the power unit 100 to catch the shelf portion of the tab 26.

Thereafter, the power unit 100 can be detached from the platform 10, via sliding bar 113, flipped over and reattached to the platform 10, again via the spline 18 and the reception slot 104 open on a second housing side plate 106 of the power unit 100, and via the tab 26, tab reception aperture 112 and sliding bar 113. The power unit 100 will then apply a bias force opposing relative pivotal movement between the first and the second struts 12, 14 in a second of two opposite directions and will aid such pivotal movement in a first of the opposite directions.

Referring now to FIG. 6, the power unit 100 further includes an externally threaded spring band 114 located about a perimeter of the torsion spring 102. The spring band 114 is fixedly attached (e.g. by pin and socket connector 116) to a second end 118 of the torsion spring 102. Further, a stationary, but axially rotatable, worm gear 120 is located about a perimeter of the spring band 114. The worm gear 120 threadably communicates with the spring band 114 to preload the torsion spring 102. In one embodiment, the torsion spring 102, the spring band 114 and the worm gear 120 are positioned in the same plane (e.g., positioned in a similar plane, perpendicular to a longitudinal axis of the reception slot 104 (and thereby the spline 18, when the assembly is in operation).

In one embodiment of the invention, the platform 10 and torsion spring 102 provide a 150 degree range of motion of the struts 12, 14. The torsion spring 102 operates over 402 degrees. The externally threaded spring band 114 includes threads over a portion of the external perimeter. Through operation of the worm gear 120, the spring band 114 provides torsion spring preload over seven (7) settings at 36 degree increments, for a total of 252 degrees. This 252 degree preload capability, plus the 150 degree operable range of motion, cover the 402 degree range of the torsion spring 102 for this certain embodiment. Multiple variations and permutations are possible.

FIGS. 7a, 7b and 7c illustrate a front, a side and an exploded view, respectively, of another embodiment of the platform of the present invention (i.e., the platform 10 shown in FIG. 1). Much of the detailed description of the component parts and functionality of the FIG. 7 platform embodiment is similar to the platform embodiment of FIGS. 2a, 2b and 3. Note that the proximal and distal struts are shown in cropped format (actual length can vary due to patient need). Table 1 provides a convenient list/explanation of component parts of the FIGS. 7a, 7b and 7c embodiment of the platform 10 of the present invention.

TABLE 1

An Embodiment of Platform 10 of the Present Invention (see FIGs. 7a, 7b, 7c)

| Component No. | Component Description |
|---|---|
| 12 | Proximal Strut - Platform |
| 14 | Distal Strut - Platform |
| 18 | Spline Driver Shaft - Platform |
| 22 | Don/Doff Lock Slide - Platform |
| 26 | Power Unit Catch - Platform |
| 28 | Range of Motion (ROM) Wheel, or ROM Gear - Platform |
| 30 | ROM Worm Gear - Platform |
| 34 | ROM Worm Gear Housing, or ROM Worm Housing - Platform |
| 35 | Platform Retainer - Platform |
| 37 | Catch Housing - Platform |
| 38 | Don/Doff Handle, or Lock Out Handle - Platform |
| 42 | Washer |
| 42A | Washer |
| 43 | Compression Spring |
| 44 | Compression Spring |
| 45 | Dowel Pin |
| 46 | Screw - e.g., Flat Head Phillips |
| 47 | Screw - e.g., Flat Head Phillips |
| 48 | Ball Bearing |
| 49 | Grooved Pin |
| 50 | Bushing - Platform |
| 52 | Stop Angle Mark(s) (SAM) |
| 53 | Power Unit Release Button |

TABLE 1-continued

An Embodiment of Platform 10 of the
Present Invention (see FIGs. 7a, 7b, 7c)

| Component No. | Component Description |
|---|---|
| 54 | End Range Tapped Holes |
| 55 | End Range Screw(s) |
| 56 | Arcuate Slot (retaining therein end range screws 55 inserted into end range tapped holes 54) |

FIGS. 8a, 8b, 8c, 8d and 8e illustrate a perspective, a top side, an edge, an opposite side, and an exploded view, respectively, of another embodiment of the power unit 100 of the present invention (i.e., the power unit 100 shown in FIG. 1). Table 2 provides a convenient list/explanation of component parts of the FIGS. 8a, 8b, 8c, 8d and 8e embodiment of the power unit 100 of the present invention. In Table 2, and in FIGS. 8a, 8b, 8c, 8d and 8e, CW stands for clockwise and CCW for counter-clockwise.

TABLE 2

An Embodiment of Power Unit 100 of the
Present Invention (see FIGS. 8a, 8b, 8c, 8d, 8e)

| Component No. | Component Description |
|---|---|
| 101 | Washer - Spring Componentry |
| 102 | Torsion Spring - Power Unit |
| 103 | Indicator Plate - CW Power Unit |
| 104 | Spline Pivot Shaft - Power Unit |
| 106 | Housing Side Plate, CCW - Power Unit |
| 107 | Indicator Plate, CCW Power Unit |
| 108 | Housing Opposite Side Plate, CW, Power Unit |
| 112 | Catch Receiver (through aperture with wall thickness) |
| 114 | Ring Gear, or Spring Band - Power Unit |
| 116 | Screw (e.g., Flat Head Socket) |
| 120 | Worm, or Worm Gear - Power Unit |
| 121 | Retaining Ring |
| 122 | Flat Washer |
| 123 | Grooved Pin |
| 124 | Tension Level Indicator |
| 126 | Assist Direction Indicator |
| 128 | Tension Adjustor Location (using Worm Gear) |

Using Embodiments of the Present Invention

Orthotic devices/braces that incorporate embodiments of the present invention are intended for therapeutic use to manage loss of motion associated with various neurological and orthopedic indications for both adults and pediatrics. Neurological indications include cerebral palsy, cerebral vascular accident, spina bifida, traumatic brain injury, brachial plexus injury, spinal cord injury, multiple sclerosis, and reflex sympathetic dystrophy. Orthopedic indications include ligament tears, tendon rupture/repair, toe walking, burns, limb loss, rheumatoid arthritis, severe fractures/trauma, arthrogryposis, muscular dystrophy, and total knee arthoplasty. Contraindications include fixed deformities.

Two primary components of the present invention are the orthotic joint (platform) and the adjustable assist unit (power unit). When incorporated into an orthosis, the platform serves as an orthotic hinge or joint with features to statically control motion. The power unit mounts to the platform and provides continuous tension to a limb to restore range of motion to the affected joint.

FIGS. 9a, 9a' and 9b illustrate a front profile, a side profile and a reverse profile of the platform 10 embodiment of FIGS. 7a, 7b, and 7c. FIGS. 10a and 10b illustrate a front profile and a reverse profile of the power unit 100 embodiment of FIGS. 8a, 8b, 8c, 8d and 8e. During use of embodiments of the present invention, FIGS. 9a, 9a', 9b, 10a and 10b show that the following components of the platform and of the power unit can at least be, and/or variously can at least provide:

Proximal Strut 12: aluminum upright bar contoured and fastened to an orthotic shell proximal to the anatomical joint;

Lock Out Handle 38: blue-colored handle used to lock the platform 10;

Power Unit Catch 26: spring loaded latch that inserts into a catch receiver 112 of the power unit 100, serving to maintain engagement between the platform 10 and the power unit 100;

Spline 18: centrally located grooved shaft that mates with the spline receiver (reception slot) 104 of the power unit 100;

Range of Motion (ROM) Wheel or Gear 28: circular ridged gear whose position can be adjusted to change extension or flexion range of motion limits;

Stop Angle Mark 52: one of two red colored reference marks located on the ROM wheel, used to gauge the angle to which the ROM wheel 28 stops at a particular range of motion of the platform 10;

Worm 30: a gear which, when turned, will change the position of the ROM wheel 28 and stop angle mark(s) 52 to set a range of motion stop for the platform 10;

Distal Strut 14: aluminum upright bar contoured and fastened to an orthotic shell distal to the anatomical joint;

Power Unit Release Button 53: allows for the power unit 100 to be detached from the platform 10 when pressed (linearly translated) in a upward direction;

Platform Retainer 35: pivot point 16 and central fastener for the platform 10; is also used with tool (jig), engaged thereon, to facilitate proper alignment of orthotic joints to one another;

End Range Tapped Holes 54: four tapped end range holes 54 (A, B, C, D) are provided (as shown in FIG. 9b) on a reverse profile of the platform 10. Each end range tapped hole 54A, 54B, 54C, 54D, is designed to receive an end range screw 55 to set up the platform 10 with a normal anatomical range of the respective joint—intended to treat and to ensure proper functioning of the power unit 100. The end range screw(s) 55 extend from respective end range tapped hole(s) 54 into an arcuate slot 56 in a member becoming the distal strut 14. One or two end range screw(s) 55 are usually used (e.g. in holes A and B; in hole C only; in hole D only). Referring to FIG. 9b, two end range screws 55 (one in each of holes A and B) are shipped pre-installed from factory. End range screws 55 in only holes A and B are recommended for ankle or wrist applications. An end range screw 55 in hole C is recommended for right knee or left elbow applications. An end range screw 55 in hole D (see FIG. 12e) is recommended for left knee or right elbow applications;

Catch Receiver 112: a through feature (aperture with wall thickness) located on a proximal aspect of the power unit 100—designed to interface with the power unit catch 26;

Tension Level Indicator 124: indicates through housing window a current tension setting of the power unit 100. Tension settings can range from a minimum of 0 to a maximum of 7, in increments of 0.5. An initial factory setting can be 1.

Spline Receiver (Reception Slot) 104: grooved (internally threaded) feature that engages the spline 18 of the platform 10;

Assist Direction Indicator 126: markings on housing of power unit (clockwise or counterclockwise) indicating a direction of the assistance generated by the power unit 100; and Tension Adjustor 128: mechanism used to increase/decrease tension generated by the power unit 100.

Locking and unlocking the platform 10 (see FIGS. 9a and 9a'). The lock out handle 38 is used to immobilize or "lockout" the platform 10, primarily for donning and doffing the orthosis with the power unit 100 attached and tensioned. In FIGS. 9a and 9a', the platform 10 is shown without the power unit 100 to better illustrate the mechanics of the locking mechanism. To use the lock out handle 38, follow these steps:

- to lock, press the lock out handle 38 downward, linearly translating the lock out handle 38 along a longitudinal axis of the proximal strut 12, until a toothed lock slide 22 (connected at a distal end of the lock out handle 38) is fully engaged with the toothed perimeter edge of the ROM wheel 28 (as shown in FIGS. 9a and 9a'); and
- to unlock, pull the lock out handle upward (proximally), linearly translating the lock out handle 38 along the longitudinal axis of the proximal strut 12 away from the ROM wheel 28, until the toothed lock slide 22 is fully disengaged from the toothed perimeter of the ROM wheel 28 (as shown in FIG. 11a).

An audible 'snap' will be heard when the lock out handle 38 is successfully locked or unlocked.

In certain embodiments of the present invention, the platform 10 can provide up to a 150° range of motion of the proximal and the distal struts 12, 14. As detailed above, and referring to FIG. 9b, initial setup for a left knee or right elbow can allow motion from 135° of flexion to 15° of hyperextension with an end range screw 55 inserted into end range tapped hole 54D (see also FIG. 12e). Initial setup for a right knee or left elbow can allow motion from 135° of flexion to 15° of hyperextension with an end range screw 55 inserted into end range tapped hole 54C. For wrist or ankle applications, initial setup having end range screws 55 inserted in each of end range tapped holes 54A and 54B allows motion from 75° of plantar (palmar) flexion to 75° of dorsiflexion. The end range screws 55 provide correct anatomical range for the joint to be treated.

FIGS. 11a, 11b and 11c illustrate how the platform 10 may be further fine-tuned to block excessive or unwanted flexion or extension, allowing for infinite positioning options between the fixed limits established by the end of range screw(s) 55 inserted into the end range tapped hole(s) 54 (A, B, C, D) and engaging the arcuate slot 56. The ROM wheel 28 includes two red colored stop angle marks (SAMs) 52 within the teeth of the ROM wheel 28. The stop angle marks 52 are most clearly visible from a side view of the platform (see FIG. 9a and 9a'). One SAM 52 corresponds to extension range limitation and the other SAM 52 to flexion range limitation. The key to success with fine tuning the platform's range of motion lies in understanding the relationship between the SAMs 52 and the proximal strut 12. Specifically, the platform's motion will stop at an angle where a SAM 52 intersects the midline of the proximal strut 12.

Note that platform 10 fine-tuning is provided to limit range of motion in either a flexion or extension direction—one cannot limit both directions simultaneously. Therefore, only one SAM 52 has significance to platform range of motion. The illustrations of FIGS. 11a, 11b and 11c show fine-tuning with the power unit 100 detached from the platform 10 (just to better illustrate the mechanics involved). However, the platform's range of motion may be fine-tuned with or without the power unit 100 attached.

To adjust the range of motion:

unlock the platform 10 (as detailed above);

the initial factory position of the platform 10 is shown in FIG. 11a. Note the position of the proximal and distal struts 12, 14 at a 180° relationship, and of the red stop angle marks (SAMs) 52 at the 5 and 7 o'clock positions. In the initial factory position (at 5 and 7 o'clock; as shown in FIG. 11a), the ROM wheel 28 does not influence the range of motion of the platform 10;

the ROM wheel 28 position is adjusted by turning the worm 30 with a ball driver 200 (see FIGS. 11b and 11c). The worm 30 may be turned in either direction; and starting at the initial factory position, depending on the direction the worm 30 is turned, one of the SAMs 52 will move into closer proximity to the proximal strut 12 compared to the other SAM 52. The "closer" SAM 52 represents the stop point. The platform 10 will not be moveable (rotatable) past the region where the SAM 52 intersects the midline of the proximal strut 12—free range of motion will be available in the other direction. FIGS. 11b and 11c illustrate two possible settings of the ROM wheel 28. In FIG. 11b, range of motion of the proximal strut 12 relative to the distal strut 14 is limited to approximately 35° in the direction (arrow) indicated. In FIG. 11c, range of motion of the proximal strut 12 relative to the distal strut 14 is limited to approximately 90° in the direction (arrow) indicated.

Figures 12A, 12B:
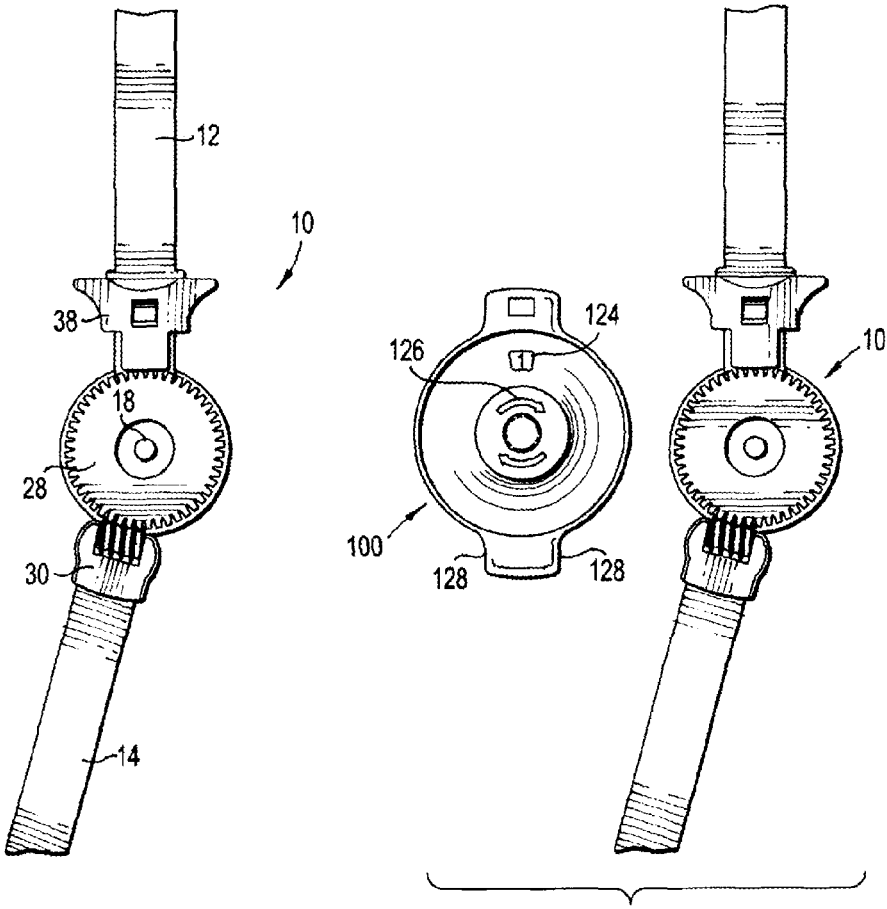
Figure 12C:
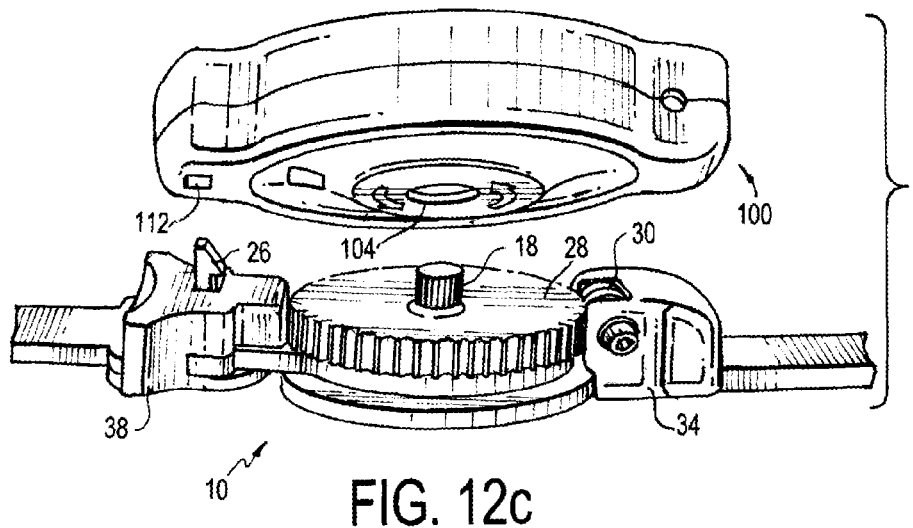
Figure 12D:
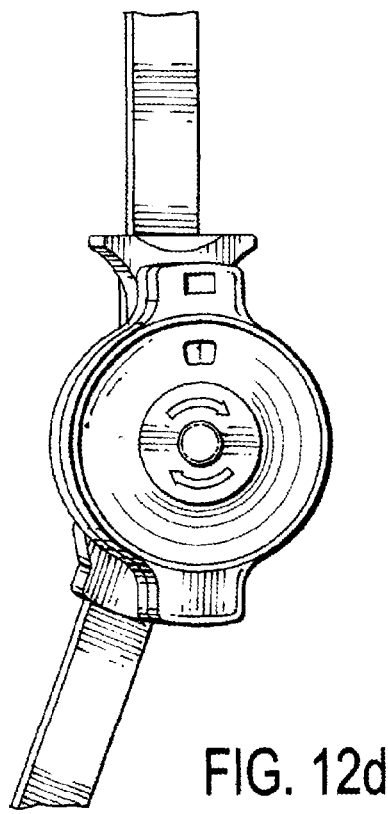
Figure 12E:
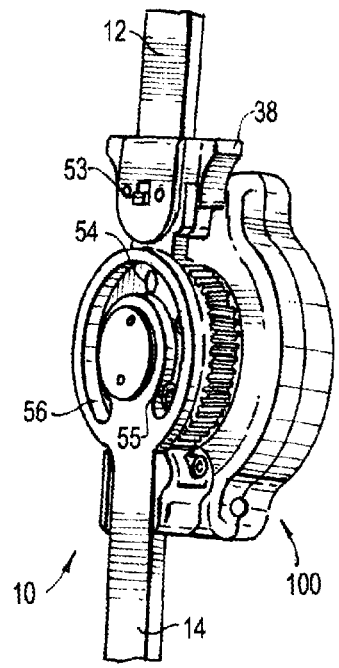

FIGS. 12a, 12b, 12c, 12d and 12e illustrate how to set up the platform 10 and attach the power unit 100 to the platform 10 for certain flexion/extension assist:

set the ROM wheel 28 to its initial factory position (as detailed above);

move the distal strut 14 of the platform 14 to the maximum end range of the direction to be assisted;

For example, to assist ankle dorsiflexion move the distal strut 14 to its maximally dorsiflexed position (+75° dorsiflexion). If the platform 10 is not moved to the maximum end range of the direction to be assisted, internal stops of the power unit 100 will limit the range of motion of the platform 10—thereby diminishing assistance output of the power unit 100.

lock the platform 10 in the position of maximum end range of the direction to be assisted. FIG. 12a shows the platform 10 oriented for right elbow extension assist (and/or left knee extension assist). As shown in FIG. 12a, maximum extension end range for an elbow setup is 15° of hyperextension;

orient the power unit 100 so the assist direction indicator 126 (on the side up, away from the platform upon attachment) shows the direction (clockwise or counterclockwise) of the motion you wish to assist. FIG. 12b shows the power unit 100 oriented to assist right elbow extension (and/or left knee extension);

line up the spline 18 and the power unit catch 26 of the platform 10 with the spline receiver (reception slot) 104 and the catch receiver 112 of the power unit as shown in FIG. 12c. Press the power unit 100 onto the platform 10. You should hear the power unit 100 catch 'click' into place upon successful latching of the power unit 100;

FIG. 12d shows a successfully attached power unit 100 to platform 10 from a top profile view; FIG. 12e shows the same, attached power unit 100 to platform 10 from a rear side profile view (also showing one end range screw 55 inserted in an end tapped hole 54 (specifically, end tapped hole 54D—see also FIG. 9b) and extending into the arcuate slot 56); and unlock the platform 10 and test the assembly, ensuring correct range of motion. For an elbow or knee assembly (as detailed above), the platform 10 should have range of motion from 135° of flexion to 15° of hyperextension—ensure that resistance is felt in correct direction To remove the power unit 100 from the platform 10:

move the lock out handle 38 of the platform 10 to the unlocked position (as detailed above);

for removal of the power unit 100 from the platform 10, the platform 10 must again be at the end range of the assisted direction. Using the lock out handle 38, lock the platform 10 in this position; and push the power unit release button 53 upward (proximally, linearly away from the pivot point—see FIG. 9b). While holding the power unit release button 53 upward (against spring bias), lift the power unit 100 off the platform 10.

The assist direction of the power unit 100 can be reversed to assist in the opposite direction. For example, a power unit 100 oriented on a platform 10 for knee extension assist could be reversed for knee flexion assist; a power unit 100 oriented on a platform 10 for wrist extension assist could be reversed for wrist palmar flexion assist, etc. To reverse the assist direction of the power unit 100 on the platform 10 (for example, here, setting the power unit 100 for flexion assist of the right elbow:

remove the power unit 100 and set the ROM wheel 28 to its initial factory position (as detailed above);

move the distal strut 14 into maximum flexion range (for a right elbow or left knee—135°);

lock the platform 10 in this position (using lock out handle 38);

orient the power unit 100 so that the assist direction indicator 126 on the side facing up (i.e., away from the platform 10 upon attachment) shows (points in) the direction (clockwise or counterclockwise) you wish to assist (here, counterclockwise for right elbow or left knee flexion force); and attach the power unit 100 to the platform 10.

To adjust the tension of the power unit 100:

the power unit 100 can be adjusted for tension between a minimum level of 0 and a maximum level of 7. In its initial factory setting, the power unit 100 has tension set at level 1 (see FIGS. 10a and 10b for tension adjuster location 138—operation of worm 120);

the power unit 100 may be adjusted for tension on or off the platform 10. Use the included Ball Driver 200 to turn the worm 120 (tension adjustor location 138) to increase/decrease the tension of the power unit 100 (torsion spring 102). The tension adjustor 138 can be approached (with the ball driver 200) from either side of the worm 120. Depending on the side of the power unit 100 (specifically, the worm 120) chosen to make the adjustment, as well as the direction of the assist selected, the tension adjustor 138 (worm 120) may require turning either toward you or away from you (clockwise or counterclockwise) to increase (decrease) the tension—watch tension level indicator 124.

to decrease the tension, simply turn the tension adjustor 138 (worm 120) in the opposite direction.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. For example, features detailed as included in certain specific embodiments above are recognized as interchangeable and possibly included in other detailed embodiments. Specific dimensions of any particular embodiment are described for illustration purposes only. It should therefore be understood that this invention is not limited to the particular embodiments described herein, but is intended to include all changes and modifications that are within the scope and spirit of the invention.

What is claimed is:

1. A hinged splint device for applying force across a body joint comprising:
    a platform including:
        a first strut and a second strut; and
        a joint assembly having a threaded spline at a pivot point thereof, the threaded spline workably fixed to one of the first strut or the second strut, the other of the first strut or the second strut having a catch located radially of the pivot point, the first strut and the second strut pivoting relative to one another about the pivot point; and
    a power unit including:
        a torsion spring; and
        a housing having an internally threaded reception slot centrally located on each of opposing housing sides of the power unit, the reception slot workably attached to a first end of the torsion spring, the housing further having a catch receiver similarly located on each of opposing housing sides of the power unit, the catch receiver workably attached to a second end of the torsion spring;
    wherein, with a first housing side exposed away from and opposite the platform, the power unit attaches to the platform to apply a bias force opposing relative pivotal movement between the first and the second struts in a first of two opposite directions, and aiding pivotal movement in a second of the opposite directions; and
    wherein, with a second housing side exposed away from and opposite the platform, the power unit attaches to the platform to apply a bias force opposing relative pivotal movement between the first and the second struts in the second of the opposite directions, and aiding pivotal movement in the first of the opposite directions.

2. The device of claim 1, wherein the power unit is detached, flipped over and reattached to the platform, without the use of tools, from the first housing side being exposed away from and opposite the platform to the second housing side being exposed away from and opposite the platform.

3. The device of claim 1, wherein points of attachment between the power unit and the platform consist only of the one centrally located reception slot on each housing side of the power unit, the one spline of the platform, the one catch receiver similarly axially located on each housing side of the power unit, and the one catch of the platform located radially of the pivot point.

4. The device of claim 1, wherein the platform further comprises an axially translatable handle that toothedly engages a gear centered about the pivot point to arrest pivotal movement of the first strut relative to the second strut.

5. The device of claim 1, wherein the power unit further comprises:
    a externally threaded spring band located about a perimeter of the torsion spring, centered about the pivot point, and workably attached to the second end of the torsion spring; and
    an axially rotatable, but otherwise fixed within the power unit housing, preload worm gear located about a perimeter of the spring band, the preload worm gear threadably communicating with the spring band to preload the torsion spring.

6. The device of claim 5, wherein the torsion spring, the spring band and the worm gear, are positioned in the same plane, the same plane being perpendicular to a longitudinal axis of the spline and the reception slot.

7. The device of claim 1, wherein the torsion spring is a circular leaf spring.

8. The device of claim 1, wherein the catch extends perpendicularly from the respective strut, and includes at a distal end thereof a lip extending perpendicularly toward the pivot point, the catch being spring biased toward the pivot point and linearly translatable along a longitudinal axis of the respective strut, wherein the catch receiver is an aperture similarly and opposingly located on each housing side of the power unit, and wherein the spring biased catch causes snap connection of the lip to the aperture when the power unit is attached to the platform.

9. The device of claim 8, wherein the platform further comprises an axially translatable handle that toothedly engages a gear centered about the pivot point to arrest pivotal movement of the first strut relative to the second strut, and wherein the catch extends perpendicularly from the respective strut from within, and is surrounded by, the axially translatable handle.

10. The device of claim 1, wherein the platform further comprises:
   a toothed range of motion (ROM) wheel mounted about the pivot point and rotatable relative to the first and the second struts; and
   an axially rotatable, but otherwise fixed within a ROM worm housing, a ROM worm gear located about a perimeter of the ROM wheel, the ROM worm gear threadably communicating with the ROM wheel to adjust a range of motion of the first strut relative to the second strut.

11. The device of claim 1, wherein the joint assembly further comprises:
   at least one end range tapped hole rotatably fixed relative to one of the first and the second struts;
   at least one end range screw, inserted into and extending from the at least one end range tapped hole; and
   an arcuate slot rotatably fixed relative to the other of first and the second struts, the at least one end range screw extending into the arcuate slot to limit range of motion the device; and
   wherein the platform provides up to a 150° range of motion of the first and the second struts.

12. The device of claim 11, wherein a position of the at least one end range tapped hole, with the at least one end range screw inserted therein, allows motion of the at least one end range screw within the arcuate slot from 135° of flexion to 15° of hyperextension, thereby providing correct anatomical range of motion for a knee.

13. The device of claim 11, further comprising a second end range tapped hole, each having a position, where, with end range screws inserted therein, allows motion of the end range screws within the arcuate slot of 75° of plantar flexion to 75° of dorsiflexion, thereby providing correct anatomical range of motion for a wrist or ankle.

14. The device of claim 11, wherein the joint assembly further comprises:
   a toothed range of motion (ROM) wheel mounted about the pivot point and rotatable relative to the first and the second struts; and
   an axially rotatable, but otherwise fixed within a ROM worm housing, a ROM worm gear located about a perimeter of the ROM wheel, the ROM worm gear threadably communicating with the ROM wheel to adjust a range of motion of the first strut relative to the second strut within the fixed limits established by the at least one end range tapped hole, the at least one end range screw, and the arcuate slot.

15. The device of claim 14, wherein the ROM wheel includes at least two stop angle marks on a perimeter thereof, one mark corresponding to an extension range limit and another mark corresponding to a flexion range limit, wherein the ROM worm gear is used to rotatably position one of the stop angle marks at an angle relative to a midline of the first strut to finely adjust device range of motion, wherein platform angular motion is limited to the angle in a respective flexion or extension range.

16. The device of claim 15, wherein the ROM worm gear functions to finely adjust device range of motion with the power unit attached to the platform.

17. A method of reversing an angular direction of force applied by a hinge assembly for an orthotic, prosthetic or rehabilitative device, where the hinge assembly comprises:
   a platform including:
      a first strut and a second strut; and
      a joint assembly having a threaded spline at a pivot point thereof, the threaded spline workably fixed to one of the first strut or the second strut, the other of the first strut or the second strut having a spring biased catch located radially of the pivot point, the first strut and the second strut pivoting relative to one another about the pivot point; and
   a power unit attached to the platform, the power unit including:
      a torsion spring; and
      a housing having an internally threaded reception slot centrally located on each of opposing housing sides of the power unit, the reception slot workably attached to a first end of the torsion spring, the housing further having a catch receiver similarly located on each of opposing housing sides of the power unit, the catch receiver workably attached to a second end of the torsion spring;
   the method comprising the steps of:
   linearly translating the catch along a longitudinal axis of the other of the first strut or the second strut, away from the pivot point and against the spring bias of the catch;
   pulling the power unit in a direction perpendicular of the first and the second struts, lifting the power unit off of the spline, detaching the power unit from the platform;
   turning the power unit over;
   threadably engaging the reception slot of the housing with the spline while aligning the catch receiver of the housing with the catch, without the use of tools, and without requiring use of any other point of attachment on or between either the platform or the power unit; and
   pressing the power unit against the platform until the spring biased catch causes snap connection of the catch to the catch receiver, thereby attaching the power unit to the platform to apply a bias force opposing relative pivotal movement between the first and the second struts in a direction opposite that of the force applied prior to turning the power unit over, and aiding pivotal movement in a direction opposite of that provided prior to turning the power unit over.

18. A hinge assembly for an orthotic, prosthetic or rehabilitative device, comprising:

a first strut and a second strut pivotally attached to one another at a pivot point;

a spline extending in a first direction perpendicularly through the first strut and the second strut and serving as the pivot point, the spline being rotatably fixed relative to one of the first strut and the second strut; and a torsion spring having a first end and a second end;

wherein the other of the first strut and the second strut has a single catch extending in the first direction, located radially of the pivot point;

wherein the first end of the torsion spring is removably attached to the extending spline and the second end of the torsion spring is removably attached to the single extending catch, the torsion spring applying a bias force opposing relative pivotal movement between the first and the second struts in a first of two opposite directions, and aiding pivotal movement in a second of the opposite directions; and wherein the torsion spring is detached from the extending spline and the single extending catch, the torsion spring turned over, and the first end of the torsion spring is again removably attached to the extending spline and the second end of the torsion spring is again removably attached to the single extending catch to then apply a bias force opposing relative pivotal movement between the first and the second struts in the second of the opposite directions, and to aid pivotal movement in the first of the opposite directions.

19. The assembly of claim 18, wherein the torsion spring is a circular leaf spring.

20. The assembly of claim 18, further comprising:

a toothed tension wheel mounted about the pivot point and rotatably fixed relative to the spline; and a axially rotatable, but otherwise fixed, worm gear located about a perimeter of the tension wheel, the worm gear threadably communicating with the tension wheel to preload the torsion spring.

* * * * *